United States Patent [19]

Prescher et al.

[11] Patent Number: 4,721,804
[45] Date of Patent: Jan. 26, 1988

[54] PROCESS FOR THE PREPARATION OF Δ 3-TETRAHYDROBENZOIC ACID- Δ 3-TETRAHYDROBENZYL ESTER

[75] Inventors: Guenter Prescher, Hanau; Andreas Grund, Darmstadt; Heinrich Petsch, Hanau; Georg Boehme, Rodenbach, all of Fed. Rep. of Germany

[73] Assignee: Degussa Aktiengesellschaft, Fed. Rep. of Germany

[21] Appl. No.: 846,689

[22] Filed: Apr. 1, 1986

[30] Foreign Application Priority Data

Apr. 25, 1985 [DE] Fed. Rep. of Germany ....... 3514938

[51] Int. Cl.$^4$ .............................................. C07C 67/44
[52] U.S. Cl. .................................................. 560/128
[58] Field of Search ................................ 560/128, 238

[56] References Cited

U.S. PATENT DOCUMENTS

| 2,698,339 | 12/1954 | Hawkins | 560/128 |
| 2,716,123 | 8/1955 | Frostick | 560/128 |
| 3,048,628 | 8/1962 | Lynn | 560/128 |
| 3,714,236 | 1/1973 | Wright | 560/238 |

OTHER PUBLICATIONS

Hester, Ind., and Eng. Chem., 51, pp. 1424–1430, (1959).
Perry, "Chemical Engineer's Handbook," 5th Ed., pp. 4–20, to 4–29 and 4–40 to 4–43, (1973).

Primary Examiner—Michael L. Shippen
Attorney, Agent, or Firm—Beveridge, DeGrandi & Weilacher

[57] ABSTRACT

The continuous preparation of Δ 3-tetrahydrobenzoic acid- Δ 3-tetrahydrobenzyl ester by reaction of 3-cyclohexene-1-carboxaldehyde is disclosed. The reaction is carried out in the presence of an aluminum mixed alcoholate, in which half of the alcohol components consists of isopropylate groups and the other half of sec-butylate groups.

11 Claims, 1 Drawing Figure

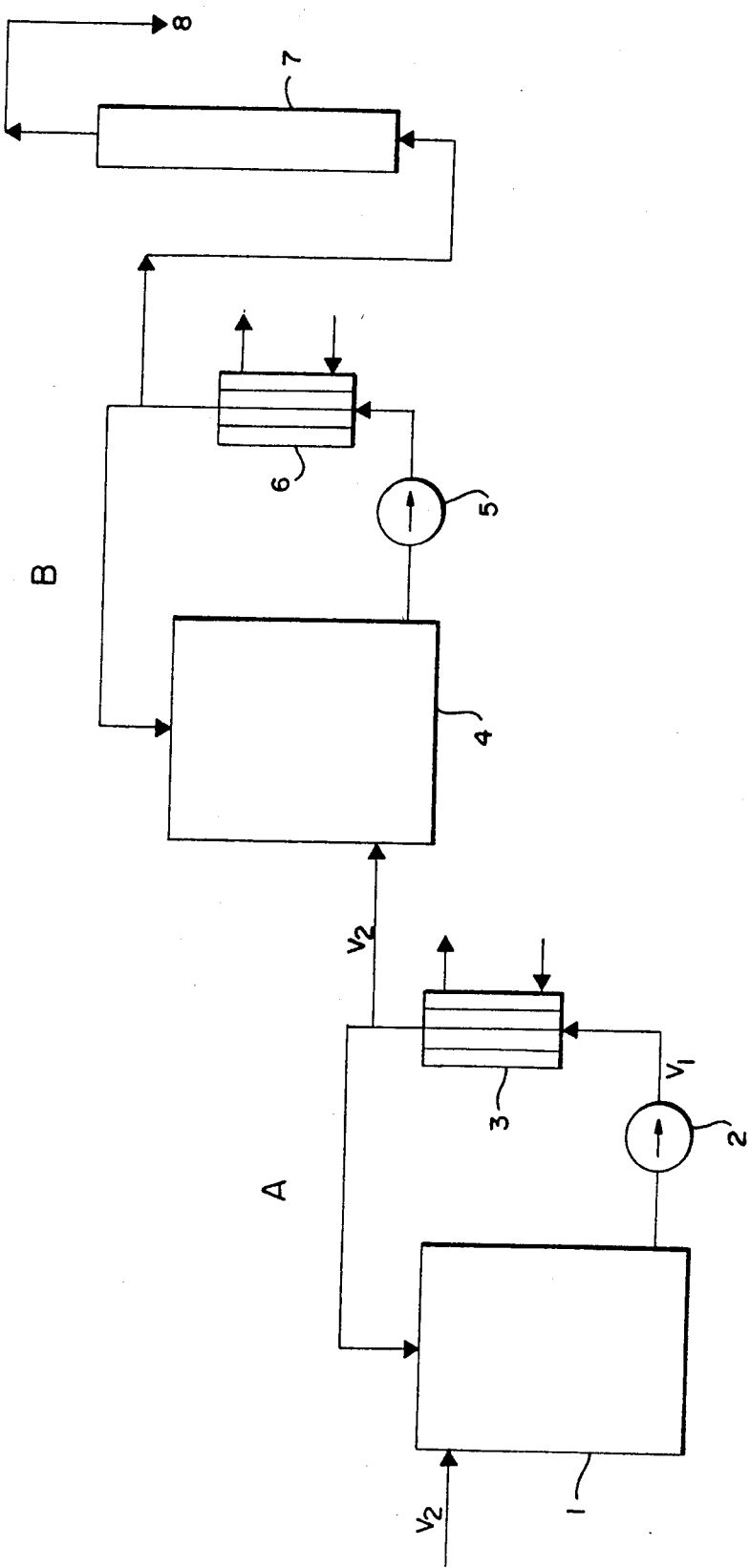

PROCESS FOR THE PREPARATION OF Δ 3-TETRAHYDROBENZOIC ACID- Δ 3-TETRAHYDROBENZYL ESTER

The present invention relates to a process for the continuous preparation of Δ3-tetrahydrobenzoic acid-Δ3-tetrahydrobenzyl ester.

It is known in the art that, in the presence of aluminum or magnesium alcoholates, aliphatic as well as aromatic aldehydes can be transformed into esters under mild conditions, and which are synthesized from an alcohol corresponding to the aldehyde and from the carboxylic acid with the same carbon skeleton. (V. Tischtschenko et al., Chem. Zentralblatt, 1309, 1554, 1556 (1906)).

U.S. Pat. No. 2,698,339 describes the preparation of Δ3-tetrahydrobenzoic acid-Δ3-tetrahydrobenzyl ester from 3-cyclohexene-1-carboxaldehyde in the presence of aluminum alcoholates. According to this patent, it is advisable to use freshly distilled aldehyde, because otherwise large amounts of catalyst are necessary with attendant lower yields.

A similar batch process is described in U.S. Pat. No. 3,048,628. Here, too, 3-cyclohexene-1-carboxaldehyde is reacted with aluminum triisopropylate, which is introduced earlier into the reactor as a highly diluted solution and is hydrolyzed with acetic acid after the reaction, whereby the resulting voluminous precipitate of aluminum hydroxide must be removed before further processing.

U.S. Pat. No. 3,709,923 (cf. P. R. Stapp, J. Org. Chem., 38, 1433 (1973)) is concerned with the preparation of Δ3-tetrahydrobenzoic acid-Δ3-tetrahydrobenzyl ester with boron-containing catalyst systems. However, since the yields are less than 79% and, moreover, the presence of a solvent is necessary, this process is not an economically feasible alternative.

Therefore, the purpose of the invention is to provide a continuous process for the preparation of Δ3-tetrahydrobenzoic acid-Δ3-tetrahydrobenzyl ester, in which 3-cyclohexene-1-carboxaldehyde that need not be freshly distilled can be used with good results.

The invention has as its object a process for the preparation of Δ3-tetrahydrobenzoic acid-Δ3-tetrahydrobenzyl ester (THB ester) by reaction of 3-cyclohexene-1-carboxaldehyde (THB) with aluminum alcoholates, and which is carried out by continuously feeding at least 90 weight percent 3-cylohexene-1-carboxaldehyde together with 0.1 to 5, preferably 0.5 to <1 weight percent, based on the aldehyde, of a liquid aluminum alcoholate or aluminum mixed alcoholate at 20° to 100° C., preferably at 30° to 50° C., into a cascade arrangement consisting of 1 to 3 reactors with quasi-complete backmixing, then feeding the reaction mixture into a flow tube at 20° to 100° C., and further processing the mixture by distillation.

The term "quasi-complete backmixing" as used herein means that no concentration gradient exists in the reactor. Preferably, 1 to 3 loop reactors are used with a recirculation ratio of 10 to 20. The expression "recirculation ratio" is understood to mean the ratio of volume per unit of time, which flows through the reactor, to volume per unit of time which is recirculated through the reactor.

Equipment suitable for carrying out the invention includes generally conventional apparatus as will be apparent to those skilled in the art. For example, vessel equipment with stirrers or circulation pumps as well as tubular reactors without any special arrangements may be used.

The invention will be further understood with reference to the drawing which shows a schematic flow diagram of the cascade of reactors with circulation pumps.

The residence time is adjusted so that the conversion of 3-cyclohexene-1-carboxaldehyde downstream of the cascade is greater than 90%, preferably greater than 95%, and after the subsequent reactor greater than 96%, preferably greater than 98%.

The reaction proceeds according to the following equation:

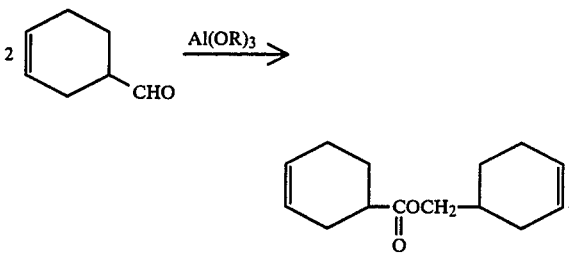

Preferably, a liquid mixed alcoholate with the formula Al(OR)$_3$ is used, half of whose alcohol components are isopropylate groups and the other half sec-butylate groups.

Unlike processes of prior art, the 3-cyclohexene-1-carboxaldehyde used in the reaction is at least 90 weight percent and need not be freshly distilled. Therefore, it is particularly advantageous to use the reaction mixture derived from the known reaction of butadiene with acrolein and consisting mainly of 3-cyclohexene-1-carboxaldehyde.

In further detail, the drawing shows a flow diagram of the reaction apparatus used in the process of the invention. Reactor loop A is composed of a reaction vessel (1) provided with backmixing capability, a pump (2) and a heat exchanger (3).

Reactor loop B is formed of a reaction vessel (4) provided with backmixing capability, pump (5) and heat exchanger (6).

The tubular reactor (7) is located downstream from reaction loop A and B and does not have any recirculation means. After passing out from tubular reactor (7), the reaction mixture proceeds to the distillation stage (8).

The recirculation ratio, U, is determined by the relationship of the flow volume passing to the heat exchanger (3) and the flow volume passing to the second reactor vessel. This ratio may be expressed by:

$$U = \frac{V_1}{V_2}$$

and is in the range of 10 to 20, wherein $V_1$ and $V_2$ are established by volume per time values.

After passing through the cascade of reactors, the conversion in the reaction mixture in terms of THB amounts to more than 95% and increases to over 98% due to the secondary reaction in the flow tube without backmixing.

Since the catalyst is sensitive to hydrolysis, care must be exercised to exclude water in the THB introduced and in the reactor gas spaces. Water free starting material is used and moisture is excluded from the reaction system. The reaction is carried out at standard pressure.

Subsequent to leaving the cascade of reactors and the tube reactor, further processing of the reaction system is carried out by distillation, for example, in a single distillation column, which is carried out at a low pressure, preferably 1–20 mbar. Lighter (lower-boiling) components are withdrawn at the top; while the main produce, THB ester, is drawn off as vapor in the side stream between the feed material and the bottom. The higher-boiling catalyst is concentrated to about 65–70% in the bottom along with heavier (higher-boiling) byproducts; the bottom product is reconcentrated by means of a thin-film evaporator to recover THB ester as long as the bottom product from the thin-film evaporator continues to flow.

The balanced total yield of THB ester, based on the THB, is 95–96%.

By way of further explanation, it is noted that the catalyst is present after the reaction with

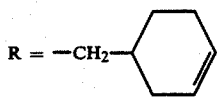

In the drawing, there is shown a reaction vessel (1) provided with pump (2) and heat exchanger (3) constituting the first circulatory reactor system and a second reactor system including vessel (4), pump (5) and heat exchanger (6). Located downstream from the circulation reactor (B) is the after reactor or tube reactor (7). The symbol "$V_2$" indicates the volume of flow to reactor (1) and to reactor (4) and the symbol "$V_1$" indicates the amount of volume leaving reactor (1). Downstream from the after reactor (7), the product goes to distillation (8). The recirculation ratio is determined by the volume ($V_1$) divided by the volume $V_2$ which should be in the range of 10 to 20. This is the ratio of volume per unit of time which flows through the reactor to the volume per unit of time which is recirculated through the reactor.

The following examples are illustrative of the invention and in each example, the mixed alcoholate consists of one-half isopropylate groups and one-half sec-butylate groups.

EXAMPLE 1

484.0 g of 3-cyclohexene-1-carboxaldehyde (98.4%) and 6.16 g of aluminum mixed alcoholate, which corresponds to 1.27 weight percent of catalyst, per hour were fed via two separate feed lines to the first agitated vessel in a two-state cascade consisting of two glass lined agitated vessels with a capacity of 560 ml and 690 ml and a series-connected tubular reactor with a volume of 260 ml. Conversions of 3-cyclohexene-1-carboxaldehyde of 95.8% were achieved in the first reactor, of 98.8% in the second reactor, and 99.7% in tubular reactor at a reaction temperature of 41° C. in the first reactor, 41° C. in the second reactor, and 43° C. in the tubular reactor. The total residence time was about 3.1 hours.

The reaction mixture emerging from the tubular reactor was fed to a distillation column (20 bubble-cap plates, DN 50) between the 10th and 11th plates. Small amounts of low-boiling distillates and unreacted 3-cyclohexene-1-carboxaldehyde reached the top of the column. Experimental conditions in the column were a bottom temperature of 200°–220° C. and a pressure of 7 mbar. The product, Δ3-tetrahydrobenzoic acid-Δ3-tetrahydrobenzyl ester, was drawn off as vapor in a side stream above the bottom; 453.2 g of 99.1% purity (GC) per hour was obtained. An additional 16.6 g (96%) of product per hour could be recovered from the bottom of the distillation column by means of a series-connected thin-film evaporator (5 mbar, 200° C.), so that the total isolated yield was 96.1%.

EXAMPLE 2

564.9 g of 3-cyclohexene-1-carboxaldehyde (94.9%) and 9.85 g of aluminum mixed alcoholate (which corresponds to 1.74 weight percent of catalyst) were fed per hour via two separate feed lines to the first agitated vessel in a two-state cascade consisting of two glass lined agitated vessels with a capacity of 560 ml and 690 ml and of a series-connected tubular reactor with a volume of 260 ml. Conversions of 3-cyclohexene-1-carboxaldehyde of 97.1% were obtained in the first reactor, of 98.9% in the second reactor, and 99.8% in the tubular reactor at a reaction temperature of 64° C. in the first reactor, 60° C. in the second reactor, and 61° C. in the tubular reactor. The total residence time was about 2.7 hours.

The reaction mixture emerging from the tubular reactor was fed to a distillation column (20 bubble-cap plates, DN 50) between the 10th and 11th plates. Small amounts of low-boiling distillates and unreacted 3-cyclohexene-1-carboxaldehyde reached the top of the column. The experimental conditions in the column were a bottom temperature of 200°–220° C. and a pressure of 7 mbar. The product, Δ3-tetrahydrobenzoic acid-Δ3-tetrahydrobenzyl ester, was drawn off as vapor in a side stream above the bottom; 487.8 g of 99.0% purity (GC) per hour was obtained. An additional 20.3 g (95%) of product per hour could be recovered from the bottom of the distillation column by means of a series-connected thin-film evaporator (5 mbar, 200° C.), so that the total isolated yield is 93.7%.

EXAMPLE 3

584.8 g of 3-cyclohexene-1-carboxaldehyde (93.6%) and 4.71 g of aluminum mixed alcoholate (which corresponds to 0.81 weight percent of catalyst) per hour were fed via two separate supply lines to the first agitated vessel in a two-stage cascade consisting of two glass lined agitated vessels with a capacity of 560 ml and 690 ml and a series-connected tubular reactor with a volume of 260 ml. Conversions of 3-cyclohexene-1-carboxaldehyde of 96.2% were achieved in the first reactor, 97.9% in the second reactor, and 99.5% in the tubular reactor at a reaction temperature of 41° C. in the first reactor, 40° C. in the second reactor, and 42° C. in the tubular reactor. The total residence time was about 2.5 hours.

The reaction mixture emerging from the tubular reactor was fed to a distillation column (20 bubble-cap plates, DN 50) between the 10th and 11th plates. Small amounts of the low-boiling distillates and unreacted 3-cyclohexene-1-carboxaldehyde reached the top of the column. The experimental conditions in the column were a bottom temperature of 200°–220° C. and a pressure of 7 mbar. The product, Δ3-tetrahydrobenzoic acid-Δ3-tetrahydrobenzyl ester, was drawn off as vapor in a side stream above the bottom; 499.7 g of 98.8% purity (GC) per hour was obtained. An additional 21.1 g (96%) of product per hour could be recovered from the bottom of the distillation column by means of a series connected thin-film evaporator (5 mbar, 200° C.), so that the total isolated yield is 93.9%.

Further variations and modifications of the invention will be apparent from the foregoing and are intended to be encompassed by the claims appended hereto.

The German priority application P3514938.8 is relied on and incorporated by reference.

We claim:

1. A process for the preparation of Δ3-tetrahydrobenzoic acid-Δ3-tetrahydrobenzyl ester comprising continuously feeding at least 90 weight percent liquid 3-cyclohexene-1-carboxaldehyde and 0.1 to 5 weight percent, based on the aldehyde, of a catalyst consisting essentially of liquid aluminum alcoholate or a liquid aluminum mixed alcoholate, at 20° to 100° C., to a reactor or a cascade of 2 to 3 reactors with recirculation of a portion of the reactor contents with essentially complete backmixing to obtain a reaction mixture, feeding said reaction mixture into a flow tube reactor at 20° to 100° C., whereby the residence time is reduced such that the conversion of 3-cyclohexene-1-carboxaldehyde downstream of the cascade is greater than 90%, and downstream of the flow tube reactor greater than 96% wherein the ratio of volume per unit of time which flows through the reactor to the volume per unit of time which is recirculated through the reactor ranges from 10 to 20.

2. The process of claim 1 further comprising subjecting the thereby obtained reaction mixture to distillation.

3. The process of claim 1, wherein an aluminum mixed alcoholate is used whose alcohol components are isopropylate and sec-butylate groups.

4. The process of claim 1, wherein the aldehyde is at a temperature of 30° to 50° C.

5. The process of claim 1, wherein the said alcoholate is at a temperature of 30° to 50° C.

6. The process of claim 1, wherein the backmixing is carried out with a recirculation count of 10 to 20.

7. The process of claim 1, wherein the aldehyde used is not freshly distilled.

8. The process of claim 1, wherein the aldehyde is in the form of the reaction mixture derived from the reaction of butadiene with acrolein.

9. The process of claim 1, wherein the aldehyde and the aluminum mixed alcohol are separately conveyed to the first reactor in the cascade and the resulting reaction mixture is then conveyed to a second reactor in the cascade and thereafter is conveyed to a tubular reactor.

10. The process of claim 9, wherein said first and second reactors are agitated and the reaction mixture is subjected to agitation.

11. The process of claim 1, wherein water is excluded from the reaction system.

* * * * *